United States Patent [19]

Krause et al.

[11] Patent Number: 5,344,995
[45] Date of Patent: Sep. 6, 1994

[54] PREPARATION OF CYCLIC ACETALS OF 3-FORMYL-2-BUTENYLTRIPHENYLPHOSPHONIUM CHLORIDE

[75] Inventors: Wolfgang Krause, Mannheim; Joachim Paust, Neuhofen; Walter Dobler, Heidelberg; Hagen Jaedicke, Ludwigshafen, all of Fed. Rep. of Germany

[73] Assignee: BASF Aktiengesellschaft, Ludwigshafen, Fed. Rep. of Germany

[21] Appl. No.: 85,903

[22] Filed: Jul. 6, 1993

[30] Foreign Application Priority Data

Jul. 14, 1992 [DE] Fed. Rep. of Germany ....... 4223061
Jul. 31, 1992 [DE] Fed. Rep. of Germany ....... 4225322

[51] Int. Cl.$^5$ .................. C07C 43/305; C07C 43/313
[52] U.S. Cl. .................................................. 568/591
[58] Field of Search ............... 568/590, 594, 596, 592, 568/591

[56] References Cited

U.S. PATENT DOCUMENTS 4,120,868 10/1978 Jaedicke et al. .......... 568/591
5,145,972 9/1992 Chabardes et al. ......... 568/590

FOREIGN PATENT DOCUMENTS 2004675 8/1971 Fed. Rep. of Germany .
1941632 12/1971 Fed. Rep. of Germany .
1312830 4/1973 United Kingdom .

OTHER PUBLICATIONS

Liebigs Ann. Chem (1976) 2194–2204.

Primary Examiner—Werren B. Lone
Attorney, Agent, or Firm—Keil & Weinkauf

[57] ABSTRACT

An improved process for preparing cyclic acetals of 3-formyl-2-butenyltriphenylphosphonium chloride by acetalization of 3-formyl-2-butenyl acetate with an aliphatic 1,3-diol, conversion of the resulting 4-acetoxy acetal into the corresponding 4-hydroxy acetal, Vilsmeier chlorination to give the corresponding 4-chloro acetal and subsequent reaction with triphenylphosphine entails carrying out the first 3 steps in an aliphatic or cycloaliphatic hydrocarbon or mixture of hydrocarbons with 6–8 carbons and the reaction with triphenylphosphine in an alkanol with 1–3 carbons and/or in aliphatic or cycloaliphatic hydrocarbon with 6–8 carbons or a corresponding mixture of hydrocarbons. The process is particularly advantageous when conversion of the 4-acetoxy acetal into the 4-hydroxy acetal is carried out with an aqueous alkali metal hydroxide solution in the presence of phase-transfer catalysts, and the first three, or all four, reaction stages are carried out in the same $C_6$–$C_8$-hydrocarbon.

6 Claims, No Drawings

PREPARATION OF CYCLIC ACETALS OF 3-FORMYL-2-BUTENYLTRIPHENYLPHOSPHONIUM CHLORIDE

The present invention relates to an improved process for preparing cyclic acetals of 3-formyl-2-butenyltriphenylphosphonium chloride starting from 3-formyl-2-butenyl acetate.

The Wittig reaction has become extremely important for the synthesis of terpenes. Thus, with its aid, total synthesis of terpenes is possible in a few stages if the carbon skeleton is built up from $C_5$ units. One example of this synthetic concept is the chain extension of polyene aldehydes using acetals of 3-formyl-2-butenyltriphenylphosphonium halides. Mention may be made of the preparation of $\beta$-apocarotenals, which are in demand as food colorants, by Wittig reaction of retinal with acetals of 3-formyl-2-butenyltriphenylphosphonium halides. This is why there has been no lack of attempts to find an advantageous process for preparing these phosphonium salts.

Thus, Liebigs Ann. Chem. (1976) 2194–2205 indicates possible ways of preparing 1,1-dimethoxy-3-methyl-2-butenyltriphenylphosphonium chloride and presents a process for preparing the considerably more suitable cyclic acetals. In the process described herein, 3-formyl-2-butenyl acetate is acetalized with 1,3-diols in toluene, the resulting acetoxy acetal is converted by transesterification with excess methanol into the corresponding hydroxy acetal, the latter is converted by Vilsmeier chlorination in benzene into the corresponding chloro acetal, and the latter is finally reacted with triphenylphosphine in toluene. The disadvantage of this process is that implementation on the industrial scale is difficult, and the yield which can be achieved are inadequate for industrial synthesis. Thus, for example, in the process described therein the solvent has to be changed for each of the 4 reaction steps, which is very costly on the industrial scale. In addition, yields of only about 44% of theory are obtained.

It is an object of the present invention to improve the process described above so that it is industrially advantageous and, moreover, the yields are considerably improved.

We have found that this object is achieved by an improved process for preparing cyclic acetals of 3-formyl-2-butenyltriphenylphosphonium chloride of the formula I

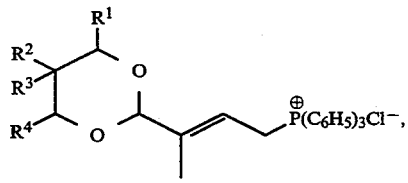

where $R^1$, $R^2$, $R^3$ and $R^4$ are each H or $CH_3$, by a) acetalizing 3-formyl-2-butenyl acetate of the formula II

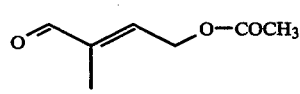

with 1,3-diols of the formula III

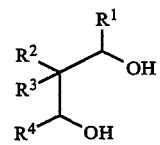

where $R^1$–$R^4$ have the abovementioned meanings, b) converting the resulting acetoxy acetals of the formula IV into the corresponding hydroxy acetals of the formula V

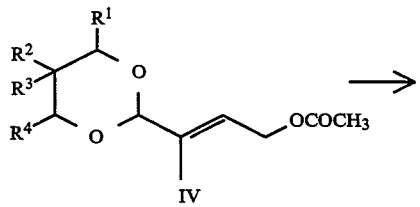

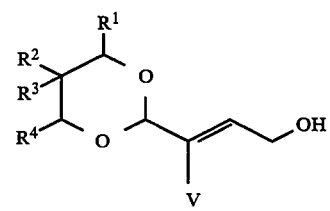

c) subjecting the resulting hydroxy acetals of the formula V to Vilsmeier chlorination to form the 4-chloro acetals of the formula VI

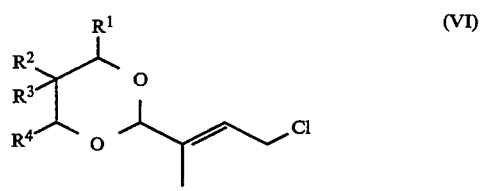

and d) reacting the 4-chloro acetals of the formula VI with triphenylphosphine, wherein steps a) to c) are carried out in an aliphatic or cycloaliphatic hydrocarbon or mixture of hydrocarbons with 6–8 carbons, and step d) is carried in an alkanol with 1–3 carbons and/or in an aliphatic or cycloaliphatic hydrocarbon with 6–8 carbons.

One advantage of this improvement in the process is that the conversion of the acetoxy acetals of the formula IV into the corresponding hydroxy acetals of the formula V can be carried out with at least 5% strength aqueous sodium hydroxide solution. The novel process is particularly advantageous when the conversion of the acetoxy acetals of the formula IV into the corresponding hydroxy acetals of the formula V is carried out with aqueous sodium hydroxide or potassium hydroxide solution in the presence of phase-transfer catalysts.

The 3-formyl-2-butenyl acetate of the formula II (also called $\beta$-formylcrotyl acetate) which is required as starting material for the process according to the invention is a known compound which plays an important part in industrial vitamin A synthesis and can be prepared as described in DE-A 20 04 675 and DE-A 19 41 632 by hydroformylation of vinylglycol diacetate.

Examples of hydrocarbons which have 6–8 carbons and are suitable for the process according to the invention are n-hexane, n-heptane, n-octane, cyclohexane and mixtures of hexanes, heptanes and/or octanes as produced by synthesis. Particular mention may be made of n-heptane and mixtures of heptanes.

Alkanols with 1–3 carbons which are suitable according to the invention are methanol, ethanol, n-propanol and isopropanol, especially methanol.

a) The acetalization of $\beta$-formylcrotyl acetate with the aliphatic 1,3-diol of the formula III is carried out according to the invention in one of the abovementioned aliphatic or cycloaliphatic hydrocarbons with 6–8 carbons as solvent. Examples of suitable acid catalysts for the acetalization are para-toluenesulfonic acid, methanesulfonic acid, trifluoromethanesulfonic acid and trichloromethanesulfonic acid.

These catalysts are added in an amount of from 0.01 to 5 mol %, preferably from 0.1 to 1.0 mol %. The water which is formed in the acetalization, and any water present in the acid used as catalyst are advantageously removed azeotropically during the reaction. If $H_2O$ is not removed, the reaction ceases at about 73% conversion.

The reaction is generally carried out at from 25 to 130° C., preferably from 40 to 100° C., under from 1 to 1013 mbar, preferably from 100 to 500 mbar. The reaction takes about 1–10, preferably 2–3, hours. The resulting organic solution of the acetal can be used as such in the subsequent synthetic steps.

b) The acetoxy acetals of the formula IV are converted into the corresponding hydroxy acetals according to the invention by reacting them in one of the abovementioned aliphatic or cycloaliphatic hydrocarbons or mixtures of hydrocarbons with aqueous sodium hydroxide or potassium hydroxide solution. The concentration of the sodium hydroxide solution should be from 3 to 52%, preferably from 20 to 50%, and that of the potassium hydroxide solution should be from 3 to 53%, preferably from 20 to 50%. The aqueous alkali metal hydroxide solution is advantageously added slowly to the reaction mixture. It is possible to shorten the reaction time, reduce the amount of alkali metal hydroxide and increase the yield by adding phase-transfer catalysts (PTC) to the reaction mixture. For detailed information on phase-transfer catalysts, reference may be made, for example, to Angew. Chem. 89 (1977) 521-33.

Examples of suitable PTCs are tetraalkylammonium salts of the formula $R_4N^{\oplus}X^{\ominus}$ where $R = C_1$–$C_{20}$-alkyl radicals, which may differ, and $X^{\ominus} = Cl^{\ominus}$, $Br^{\ominus}$ or $I^{\ominus}$, in particular Protectol• (BASF; benzyl-$C_{12}$-$C_{14}$-alkyldimethylammonium chloride) and Aliquat• (General Mills, Inc., Minneapolis, USA). The reaction is generally carried out at from 20° to 80° C., preferably from 30° to 50° C. The reaction time depends on the temperature and the alkali concentration and is 1–10, preferably 2–4, hours. When a PTC is used, the amount of NaOH or KOH necessary for the reaction is reduced by a factor of 2–10 from the amounts otherwise required.

The ratio of organic phase to aqueous phase should be about 1:4 to 10:1, preferably 1:1 to 7:1.

Since the reaction mixture does not separate satisfactorily into two phases at room temperature, the phase separation is carried out at about 40°–50° C., preferably immediately after completion of the reaction. The organic phase is separated off and then subjected to azeotropic distillation to remove water. A hydrolysis of this type in a two-phase system using phase-transfer catalysts has not to our knowledge been described previously.

c) The Vilsmeier chlorination is generally carried out in a conventional way by first preparing the Vilsmeier complex by slowly adding $SOCl_2$ or $COCl_2$ to a mixture of dimethylformamide (DMF) and the hydrocarbon according to the invention at from 0 to 20° C., preferably from 3° to 10° C. Then, at from 0 to 20° C., preferably about 3°–10° C., the above-described crude solution of hydroxy acetal of the formula V is added over the course of 0.5–10 hours, preferably about 1–3 hours. Care must be taken to stir this solution during the addition because phase separation may easily occur. After subsequent reaction for from 0.5 to 10, preferably from 1 to 3, hours, the lower phase is separated off and extracted several times with the hydrocarbon according to the invention, and the combined organic phases are treated with aqueous alkali metal hydroxide solution or water and then washed with dilute alkali metal hydroxide solution or water.

Optimal yields are achieved by using for the Vilsmeier chlorination according to the invention DMF and $SOCl_2$ or $COCl_2$ in the molar ratio from 7:1 to about 2:1. The required amount of DMF is generally from 2.0 to 10, preferably from 2.5 to 4.0 mol per mol of the hydroxy acetal of the formula V. The hydrocarbon or mixture of hydrocarbons is advantageously used in amounts of about 300–1500 ml, preferably 500–1100 ml, of solvent per mol of hydroxy acetal of the formula V.

The combined organic extracts are washed with preferably 10% strength alkali metal hydroxide solution and water.

Particularly important for the process according to the invention is the surprisingly advantageous reaction of the 4-chloro acetals of the formula VI with triphenylphosphine, which, when carried out in toluene according to the prior art, gives yields of only 65% of theory. This reaction can be carried out according to the invention either in an alkanol with 1–3 carbons or in a hydrocarbon or mixture of hydrocarbons with 6–8 carbons, which is preferably the same as in the other reaction stages. However, it is also possible and advantageous to use mixtures of an alkanol with 1–3 carbons and a hydrocarbon with 6–8 carbons. In the presence of an alkanol there is a drastic reduction in the times necessary for complete reaction.

d) The reaction with triphenylphosphine is carried out by distilling the solution obtained in stage c) to remove the solvent, entirely or only partially under reduced pressure, dissolving the residue in methanol, adding triphenylphosphine to the solution, and refluxing until salt formation is complete.

The amount of $C_1$–$C_3$-alkanol used for this is from 100 to 1000 ml, preferably from 250 to 500 ml, per mol of 4-chloro acetal of the formula VI, and that of triphenylphosphine is about 1–1.5 mol per mol of 4-chloro acetal of the formula VI. The reaction takes about 2–8 hours. It is possible in this way to prepare, for example, 3-formyl-2-butenyltriphenyl-phosphoniumchloride in 92% yield from a 4-chloro acetal of the formula VI.

It was surprising that reaction d) takes place so advantageously in lower alkanols, especially methanol, as the solvent because it might have been expected that the 4-chloro acetal of the formula VI would at least in part be converted by the alkanol into the 4-alkoxy acetal.

The reaction with triphenylphosphine in a $C_6$–$C_5$-hydrocarbon is advantageously carried out by adjusting the solution of the 4-chloro acetal of the formula VI obtained in stage c) to a concentration of about 10–50%, preferably 30–40%, and heating to boiling. The triphenylphosphine is then added to the mixture, which is refluxed until salt formation is complete. The amount of triphenylphosphine is generally from 1 to 1.5 mol per mol of 4-chloro acetal. However, it is also possible first to add triphenylphosphine to the 4-chloro acetal solution which has been adjusted to a suitable concentration, and then to heat to boiling. The reaction takes from 6 to 36 h, preferably from 8 to 24 h. Yield: 95% from 4-chloro acetal VI.

It was surprising that it was possible by replacing the toluene used as solvent in the prior art by an aliphatic hydrocarbon considerably to increase the yields obtainable.

Using the process according to the invention, especially the particular procedure for converting the 4-acetoxy acetals of the formula IV into the 4-hydroxy acetals of the formula V, and for the reaction with triphenylphosphine, it is possible to prepare in a relatively straightforward way even on the industrial scale, and with extremely good overall yields, the cyclic acetals of 3-formyl2-butenyl-triphenylphosphonium chloride which are in great demand for terpene syntheses.

EXAMPLE 1 a) 213.2 g (2.005 mol) of neopentyl glycol were suspended at room temperature (RT) in 1.6 l of n-heptane, and 288.1 g (2 mol) of (E)-3-formyl-2-butenyl acetate were added. The pressure in the reaction vessel was then adjusted to about 200 mbar, the mixture was heated to 40° C., and then a solution of 0.76 g (4 mmol) of p-toluenesulfonic acid (hydrate) in 0.76 g of water was added all at once. The reaction mixture was heated to 55°–60° C., and an azeotrope boiling at 40°–50° C. was distilled out. The reaction mixture had become clear after about 35 minutes (min), and 36.5 ml of water had been collected after about 2 hours (h).

b) The solution from stage a) was cooled to 40° C., 2 ml of Protectol• KLC-50 (50% strength solution in water) were added, and 240 g (3 mol) of a 50% strength aqueous NaOH solution ($\delta = 1.52$) were added over the course of 1 h. The mixture was then stirred at 40°–45° C. for 2 h, 180 ml of water were added, and the mixture was stirred for a further 10 min. The two phases separated well at 45°–50° C. The organic phase was separated off and then subjected to azeotropic distillation at 58° C./193 mbar to remove water.

c) 600 ml of dimethylformamide (DMF) and 600 ml of n-heptane were cooled to 5° C. and, at 5°–10° C., 297.4 g (2.5 mol) of $SOCl_2$ were added over the course of 1 h, during which the Vilsmeier complex precipitated. The mixture was stirred for 30 min and then, at 0°–5° C., the crude (E)-3-(5,5-dimethyl-1,3-dioxan-2-yl)-2-buten-1-ol obtained in stage b) was added over the course of 2 h from a stirred dropping funnel (because of phase separation in n-heptane), and then reaction was allowed to continue at 0°–5° C. for 1 h. For workup, the lower phase was separated off and extracted with 3×300 ml of n-heptane, stirring for 15 min, the combined organic phases were washed with a mixture of 600 g of 10% strength aqueous NaOH and 375 ml of water and then stirred for 15 min, the phases were separated, and the organic phase was washed at 5°–10° C. with a mixture of 110 g of 50% strength aqueous NaOH and 440 ml of water. Finally, the organic phase was washed 3 times with 300 ml of water each time.

The yield was 2290.6 g of a 14.8% by weight solution of (E)-2-(3-chloro-1-methyl-1-propenyl)-5,5-dimethyl-1,3-dioxane in n-heptane, corresponding to 339 g calculated as 100% (1,656 mol), corresponding to a yield of 82.8% based on (E)-3-formyl-2-butenyl acetate (II).

d) About 82–87% of the heptane was distilled out at 60° C. under 100 mbar from the solution obtained as in Example 1c), the residue was dissolved in 550 ml of methanol, 434.1 g (1.656 mol) of triphenylphosphine were added, and the mixture was refluxed for 2 h.

The yield was 1218 g=1221.7 ml of a solution containing 0.2% water and 67% solid (90% purity). Titration showed that the solution contained 1.58 mol of (E)-3-(5,5-dimethyl-1,3-dioxan-2-yl)-2-butenyltri-phenylphosphonium chloride, corresponding to a yield of 78.8% based on II. The product is in the form of a mixture of about 10 parts of the E isomer and 1 part of the Z isomer.

EXAMPLE 2

About 50% of the heptane was distilled out at 60° C./100 mbar from the solution obtained as in example 1c). 434.1 g (1,656 mol) of triphenylphosphine were added to this concentrated solution, and the mixture was refluxed for 16 h. After the reaction was complete, 500 ml of methanol were added at 30° C., the mixture was stirred thoroughly, and the phases were separated. The methanolic solution (1160 g) contained 64% of (E)-3-(5,5-dimethyl-1,3-dioxan-2-yl)-2-butenyltri-phenylphosphonium chloride, corresponding to 1.59 mol=79.6% yield based on 3-formyl-2-butenyl acetate.

EXAMPLE 3 a) Acetalization of II with neopentyl glycol in heptane 319.7 g (3.01 mol) of neopentyl glycol were suspended in 2.5 l of n-heptane at RT, and 432 g (3 mol) of (E)-3-formyl-2-butenyl acetate (99% pure) were added. The pressure in the reaction vessel was then adjusted to about 300 mbar, the mixture was heated to 40° C., and then a solution of 1.14 g (6 mmol) of p-toluenesulfonic acid hydrate in 1.14 g of water was added all at once. The mixture was then heated at 53°–62° C. under 313–277 mbar for 3 h, during which 53 ml of water were removed azeotropically. Analysis by gas chromatography showed that the yield of (E)-2-(3-acetoxy-1-methyl-1-propenyl)-5,5-dimethyl-1,3-dioxane (IVa) was 98.9% of theory.

b) Hydrolysis of IVa without phase-transfer catalyst (PTC)

A total of 280 ml (10.64 mol) of 50% strength aqueous NaOH was added over the course of 2 h at 40°–50° C. with stirring to the crude solution of the compound IVa obtained in Example 3a. Subsequently 560 ml of water were added, the mixture was stirred for 15 min and, after settling for 30 min, the lower phase was separated off. A further 280 ml (10.64 mol) of 50% strength aqueous NaOH were added to the heptane phase at 40°-50° C. over the course of 15 min and, after the end of the addition, 560 ml of water were added, the mixture was stirred for a further 15 min and, after settling for 30 min, the lower phase was separated off.

The heptane phase was not washed, and water was removed at 46°-51° C. under 260-200 mbar. Concentration of the heptane phase resulted in 542.3 g of residue containing 85% by weight of (E)-2-(3-hydroxy-1-methyl-1-propenyl)-5,5-dimethyl-1,3-dioxane (Va) corresponding to a yield of 82.5% of theory based on compound II.

EXAMPLE 4

Hydrolysis of VIa with PTC 115.75 g (0.5 mol) of (E)-2-(3-acetoxy-1-methyl-1-propenyl)-5,5-dimethyl-1,3-dioxane (IVa) prepared as in Example 3a were dissolved in 400 ml of n-heptane at RT, the solution was heated to 40° C., 0.25 ml of Aliquat• was added, and then 60 g (0.75 mol) of 50% strength aqueous NaOH were added over the course of 5 min. The mixture was then stirred at about 45° C. for about 2 h, during which temperatures of 55°-60° C. occurred transiently without heating or cooling.

For workup, 90 ml of water were added to the mixture while stirring vigorously, and the mixture was stirred at 44° C. for about 5 min. In order to obtain two clear phases, the mixture was briefly heated to 60° C., at which phase separation took place. The hot heptane phase was evaporated to result in 92.53 g of Va (99% pure), corresponding to a yield of 98.3% based on compound IVa, or 97.3% based on compound II. The cis/trans ratio in the resulting compound Va was about 1:4.

EXAMPLE 5

Vilsmeier chlorination of compound Va 285 ml (270.75 g=3.7 mol) of DMF were mixed with 750 ml of n-heptane at RT, the mixture was cooled to 0° C. and, at 0°-5° C., 138.2 g (1.15 mol) of $SOCl_2$ were added over the course of 30 min, during which the Vilsmeier complex precipitated. The mixture was then stirred for 10 min and subsequently, at 0°-5° C., a stirred emulsion of 192 g (1 mol) of the compound Va (97% pure) in 800 ml of n-heptane was added over the course of 45 min, and the mixture was left to react at this temperature for 2 h.

For workup, 1420 g (3.55 mol) of 10% strength aqueous NaOH were added dropwise at 10°-15° C. over the course of 1.5 h and the mixture was then stirred for 5 min. After phase separation, the organic phase was washed with 250 ml of water. 1227.2 g of a 14.7% by weight solution of 2-(3-chloro-1-methyl-1-propenyl)-5,5-dimethyl-1,3-dioxane (VIa) in heptane were obtained, corresponding to a yield of 88.1% of theory based on Va.

EXAMPLE 6

285 ml of DMF and 750 ml of n-heptane were mixed at RT and cooled to 0° C. and, at 0°-5° C., 138.2 g of $SOCl_2$ were added over the course of 30 min, the mixture was stirred for a further 10 min and then, at 0°-5° C., a stirred emulsion of 192 g (1 mol) of the compound Va (97% pure) in 800 ml of n-heptane was added over the course of 45 min. The mixture was left to react at this temperature for a further 2 h (conversion complete according to TLC).

For workup, the lower phase was separated off and extracted with 3×150 ml n-heptane, the combined organic phases were cooled to 5° C. and then a mixture of 275 ml of 10% strength aqueous NaOH and 190 ml of water was added over the course of 15 min. After 15 min at 5°-10° C., the lower phase was separated off and the NaOH wash of the organic phase was repeated.

Finally, the organic phase was washed with 3×150 ml of water.

1877.4 g of a 10.41% by weight solution of 2-(3-chloro-1-methyl-1-propenyl)-5,5-dimethyl-1,3-dioxane (VIa) in heptane remained, corresponding to a yield of 95.5% of theory based on compound Va.

EXAMPLE 7 ( REACTION WITH PHOSGENE )

a) 213.2 g (2.005 mol) of neopentyl glycol were suspended in 1.6 l of n-heptane at RT, and 288.1 g (2 mol) of (E)-3-formyl-2-butenyl acetate were added. The pressure in the reaction vessel was then adjusted to about 200 mbar, the mixture was heated to 40° C., and then a solution of 0.47 g (5 mmol) of methanesulfonic acid in 0.47 g of water was added all at once. The reaction mixture was heated to 60° C., and an azeotrope boiling at 40°-50° C. was distilled out. The reaction mixture had become clear after about 30 minutes, and 36 ml of water had been collected after about 2.5 (h).

b) The solution from stage a) was cooled to 40° C. and 2 ml of a 25% strength solution of hexadecyltrimethylammonium chloride in water were added, and 240 g (3 mol) of 50% strength aqueous NaOH ($\delta=1.52$) were added over the course of 1 h. The mixture was then stirred at 40°-45° C. for 2 h, 180 ml of water were added, and stirring was continued for 10 min. The two phases separated well at 45°-50° C. The organic phase was separated off and then subjected to azeotropic distillation at 58° C./200 mbar to remove water.

c) 500 ml of DMF and 600 ml of n-heptane were mixed at 5° C. and, at 5°-10° C., 247.5 g (2.5 mol) of $COCl_2$ cooled to −5° C. were added over the course of 1 h, during which the Vilsmeier complex precipitated. The mixture was then stirred for 30 min and, at 0°-5° C., the crude (E)-3-(5,5-dimethyl-1,3-dioxan-2-yl)-2-buten-1-ol obtained in stage b) was added from a stirred dropping funnel over the course of 2 h, and the mixture was left to react at 0°-5° C. for a further 1 h. For workup, the lower phase was separated off and extracted with 4×200 ml of n-heptane, stirring for 15 min, the combined organic phases were washed with a mixture of 300 ml of 5% strength aqueous NaOH and 375 ml of water and then stirred for 15 min, the phases were separated, and the organic phase was washed at 5°-10° C. 3 times with 300 ml of water each time.

The yield was 2153 g of a 15.8% by weight solution of (E)-2-(3-chloro-1-methyl-1-propenyl)-5,5-dimethyl-1,3-dioxane in n-heptane, corresponding to 340 g calculated as 100% (1.66 mol), corresponding to a yield of 83% based on (E)-(3-formyl-2-butenyl acetate (II).

d) About 50% of the heptane was distilled out at 60° C. under 100 mbar from the solution obtained in stage c), 435 g (1.66 mol) of triphenylphosphine were added to the residue, and the mixture was refluxed for 20 h. After cooling to room temperature, 600 ml of MeOH were added, the mixture was vigorously stirred and the phases were separated to result in 1293 g of a methanolic solution containing 0.2% water and 62% solid (95% purity). Titration showed that the solution contained 1.6 mol of (E)-3-(5,5-dimethyl-1,3-dioxan-2-yl)-2-butenyl-triphenylphosphonium chloride, corresponding to a yield of 80% based on 3-formyl-2-butenyl acetate. The compound is in the form of a mixture of about 10 parts of the E isomer and 1 part of the Z isomer.

EXAMPLE 8

About 50% of the heptane was distilled out at 60° C. under 100 mbar from a solution obtained as in Examples 7a to 7c, 435 g (1.66 mol) of triphenylphosphine and 600 ml of methanol were added to the residue, and the mixture was refluxed for 2 h. After cooling to RT, the phases were separated to result in 1290 g of a methanolic solution containing 0.2% water and 62% solid (95% purity). Titration showed that the solution contained 1.6 mol of (E)-3-(5,5-dimethyl-1,3-dioxan-2-yl)-2-butenyl-triphenylphoshoniumchloride, corresponding to a yield of 80% based on 3-formyl-2-butenyl acetate. The compound is in the form of a mixture of about 10 parts of the E isomer and 1 part of the Z isomer.

EXAMPLE 9

About 70% of the heptane was distilled out at 60° C./100 mbar from a solution obtained as in Example 1c. 434.1 g (1,656 mol) of triphenylphosphine and 600 ml of ethanol were added to this concentrated solution, and the mixture was refluxed for 2.5 h. After the reaction was complete, the phases were separated out at 30° C. The ethanolic solution (1250 g) contained 59% of (E)-3-(5,5-dimethyl-1,3-dioxan-2-yl)-2-butenyltriphenylphosphonium chloride, corresponding to 1.58 mol=79% yield based on 3-formyl-2-butenyl acetate.

We claim:

1. An improved process for preparing cyclic acetals of 3-formyl-2-butenyltriphenylphosphonium chloride of the formula I

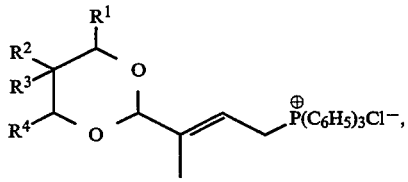

where $R^1$, $R^2$, $R^3$ and $R^4$ are each H or $CH_3$, comprising
a) acetalizing 3-formyl-2-butenyl acetate of the formula II

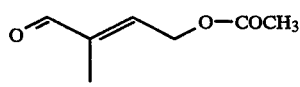

with 1,3-diols of the formula III

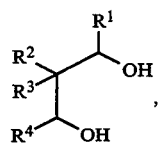

where $R^1$, $R^2$, $R^3$ and $R^4$ have the abovementioned meanings,
b) converting the resulting acetoxy acetals of the formula IV into the corresponding hydroxy acetals of the formula V

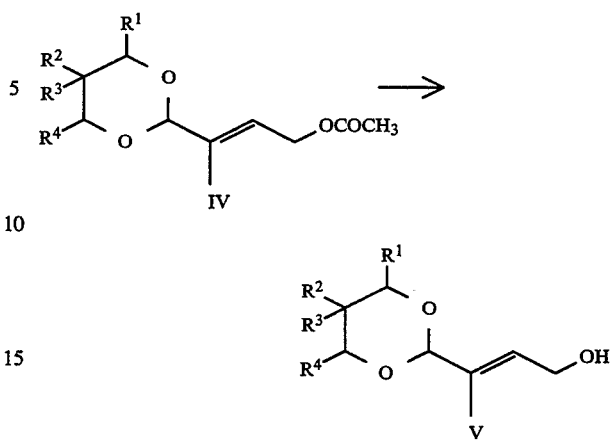

by treating the acetoxy acetal with aqueous sodium hydroxide or potassium hydroxide solution,
c) subjecting the resulting hydroxy acetals of the formula V to Vilsmeier chlorination to form the 4-chloro acetals of the formula VI

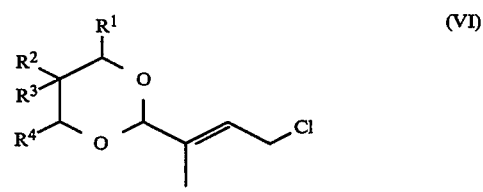

and
d) reacting the 4-chloro acetals of the formula VI with triphenylphosphine,
wherein steps a) to c) are carried out in an aliphatic or cycloaliphatic hydrocarbon or mixture of hydrocarbons with 6–8 carbons, and step d) is carried out in an alkanol with 1–3 carbons, in an aliphatic or cycloaliphatic hydrocarbon with 6–8 carbons, a mixture of an alkanol with 1–3 carbons and an aliphatic or cycloaliphatic hydrocarbon with 6–8 carbons, or in a mixture of hydrocarbons with 6–8 carbons.

2. The process of claim 1, wherein steps a) to c) or a) to d) are carried out in the same hydrocarbon or mixture of hydrocarbons.

3. The process of claim 1, wherein the conversion of the acetoxy acetals of the formula IV into the corresponding hydroxy acetals of the formula V in step b) is carried out with at least 5% strength aqueous sodium hydroxide or potassium hydroxide solution.

4. The process of claim 3, wherein the conversion of the acetoxy acetals of the formula IV into the corresponding hydroxy acetals of the formula V in step b) is carried out with aqueous sodium hydroxide or potassium hydroxide solution in the presence of phase-transfer catalysts.

5. The process of claim 1, wherein the reaction in step d) of the 4-chloro acetals of the formula VI with triphenylphosphine is carried out in a mixture of methanol and an aliphatic or cycloaliphatic hydrocarbon or mixture of hydrocarbons with 6–8 carbons as solvent.

6. An improved process for preparing cyclic acetals of 3-formyl-2-butenyltriphenylphosphonium chloride of the formula I

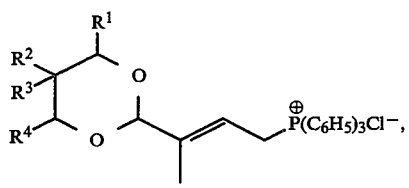
where $R^1$, $R^2$, $R^3$ and $R^4$ are each H or $CH_3$, which comprises reacting the 4-chloro acetals of the formula VI
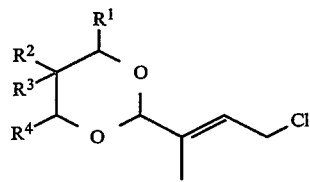
with triphenylphosphine in an alkanol with 1–3 carbons, in an aliphatic or cycloaliphatic hydrocarbon with 6–8 carbons, or in a mixture of an alkanol with 1–3 carbons and an aliphatic or cycloaliphatic hydrocarbon with 6–8 carbons, as solvent.
* * * * *